United States Patent [19]

Boswell, Jr. et al.

[11] 4,241,065
[45] Dec. 23, 1980

[54] FLUORO ANALOGS OF HYDROCODONE AND OXYCODONE USEFUL AS ANALGESICS, NARCOTIC ANTAGONISTS OR BOTH

[75] Inventors: George A. Boswell, Jr.; Rosetta M. Henderson, both of Wilmington, Del.

[73] Assignee: E. I. Du Pont de Nemours and Company, Wilmington, Del.

[21] Appl. No.: 54,225

[22] Filed: Jul. 2, 1979

Related U.S. Application Data

[63] Continuation-in-part of Ser. No. 944,197, Sep. 19, 1978, abandoned.

[51] Int. Cl.$^3$ .................. A61K 31/485; C07D 489/00
[52] U.S. Cl. .......................................... 424/260; 546/46
[58] Field of Search ...................... 546/46, 74; 424/260

[56] References Cited

U.S. PATENT DOCUMENTS

| | | | |
|---|---|---|---|
| 3,137,701 | 6/1964 | Ayer | 546/46 |
| 3,332,950 | 7/1967 | Blumberg et al. | 546/45 |
| 3,393,197 | 7/1968 | Pachter et al. | 546/44 |
| 3,928,359 | 12/1975 | Walther et al. | 546/45 |
| 3,976,691 | 8/1976 | Middleton | 260/544 F |
| 4,089,855 | 5/1978 | Chatterjie et al. | 546/44 |

OTHER PUBLICATIONS

Somogyi, et al., Chemical Abstracts, vol. 87, 168240y, (1977).
Bognar, et al., Chemical Abstracts, vol. 77, 19840k, (1972).
Makleit, et al., Chemical Abstracts, vol. 77, 152405p, (1972).
Makleit, et al., Chemical Abstracts, vol. 84, 90359k, (1976).
Bognar, et al., Chemical Abstracts, vol. 73, 131174q, (1970).
Yeh, et al., Journal of Pharmaceutical Sciences, vol. 65, No. 6, pp. 902–904, (1976).
Bognar, et al., Acta Chimica Academiae Scientiarum Hungaricae, vol. 67, (1), pp. 63–69, (1971).
Stork, J. Am. Chem. Soc., vol. 78, pp. 4619–4621, (1956).
Somogyi, et al., Acta Chimica Academiae Scientiarum Hungaricae, vol. 97, pp. 339–344, (1978).

Primary Examiner—Donald G. Daus
Assistant Examiner—Diana G. Rivers

[57] ABSTRACT

6-Fluoro analogs of hydrocodone and oxycodone are analgesics and/or narcotic antagonists. Exemplary are 17-cyclopropylmethyl-4,5-epoxy-6,6-difluoro-3-methoxymorphinan and 17-cyclopropylmethyl-6,7-didehydro-4,5-epoxy-6-fluoro-3-methoxy- and -3-acetoxymorphinan.

19 Claims, No Drawings

FLUORO ANALOGS OF HYDROCODONE AND OXYCODONE USEFUL AS ANALGESICS, NARCOTIC ANTAGONISTS OR BOTH

CROSS-REFERENCE TO RELATED APPLICATION

This is a continuation-in-part of application Ser. No. 944,197 filed Sept. 19, 1978 and now abandoned.

DESCRIPTION

1. Technical Field

This invention relates to fluorine analogs of hydrocodone and oxycodone and their analgesic and/or narcotic antagonist properties in mammals.

2. Background Art

Morphine and codeine analgesics exhibit toxic properties or have addictive action. Considerable effort has been made to find derivatives that are free from these qualities and still have analgesic effects. Compounds which are narcotic antagonists are also useful in medicine, such as treatment of addicts.

Fluorine derivatives of codeine have been reported by Ayer U.S. Pat. No. 3,137,701 from the reaction of a 6-hydroxyalkaloid having the codeine ring structure with a fluorinating agent such as N-(2-chloro-1,1,2-trifluoroethyl)diethylamine. The compound obtained by Ayer, and confirmed by Bognar et al., Acta Chimica Academiae Scientiarum Hungaricae 67, 63–69 (1971), has the formula

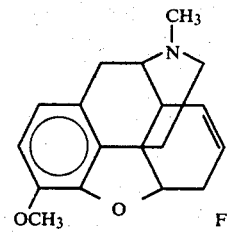

wherein the double bond is at the 7,8 carbon position, i.e. beta-gamma, relative to fluorine in the 6-position. It is well-known that fluorine substitution in organic compounds causes different biological effects and is different from chlorine, bromine or iodine substitution, as for example the 6-chloro, 7-8 double bond compound disclosed by Storch et al., J. Am. Chem. Soc. 78, 4619 (1956).

DISCLOSURE OF THE INVENTION

A compound of the formula

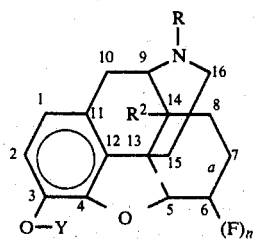

where

R is selected from the group consisting of hydrogen, alkyl of 1-10 carbons, allyl, methylallyl, dimethylallyl, cycloalkylmethyl of 4-7 carbon atoms, 2-furanylmethyl, 2-tetrahydrofuranylmethyl, 2-thienylmethyl, 2-thienylethyl and phenylethyl which may be ring substituted with chloro, bromo, fluoro, methoxy or 1-3 carbon alkyl substituents;

Y is H or R';

R' is selected from the group consisting of alkyl of 1-4 carbons and alkanoyl of 1-12 carbons;

$R^2$ is selected from the group consisting of hydrogen, hydroxy and alkanoate of 1-4 carbons;

n is 1 or 2; and a is a 6,7 double bond when n=1, and a single bond when n=2;

and pharmaceutically acceptable salts of the compound.

Formula I and all formulas shown hereinafter are depicted by planar representations. One skilled in the art will readily understand the nonplanar aspects of these representations, for example, that the carbon-oxygen bond in the 5-position is exo or alpha.

Pharmaceutically acceptable salts are those made with physiologically acceptable acids that are known in the art; such salts include hydrochloride, sulfate, phosphate, nitrate, citrate, maleate, and the like. The invention also includes pharmaceutically active compositions of these compounds.

Particularly preferred are compounds of formula I where R is cyclopropylmethyl and cyclobutylmethyl. Those compounds wherein Y is H or acetyl are generally more active as are those where $R^2$ is H. For reasons of availability and pharmacological activity, n is 1 and a is a double bond. The compounds of Examples 5–7, 11 and 12 illustrate the best mode of the invention of which Example 11 is preferred.

Compounds of this invention can be prepared by reacting a disubstituted aminosulfur trifluoride with an acid salt (MA) of a 6-keto compound corresponding to that of formula I wherein a is a single bond and $(F)_n$ is replaced by carbonyl oxygen (=O). When R is H (obtained as shown in Example 13), the corresponding 6-fluorides are converted to pharmaceutically superior compounds by alkylation of the NH group with RX usually under basic conditions where R is as previously defined except that it is not H and X is generally halogen (Cl, Br or I) e.g., as cyclopropylmethyl bromide. The more active compounds are preferably prepared by reacting under substantially anhydrous conditions as ketone having the formula

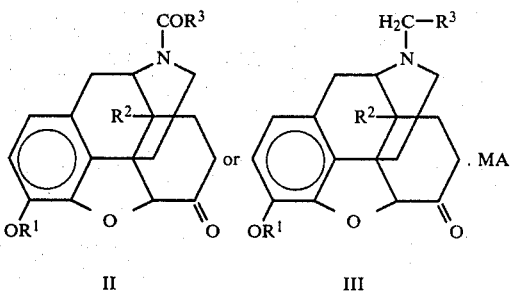

wherein $R^3$ is selected from the group consisting of alkyl of 1-9 carbons, vinyl, 1-propenyl, isobutenyl, cycloalkyl of 3-6 carbon atoms, 2-furanyl, 2-tetrahydrofuranyl, 2-thienyl, 2-thienylmethyl and phenylmethyl which may be ring substituted with chloro, bromo, fluoro, methoxy or 1-3 carbon alkyl substituents;

$R^1$ and $R^2$ are as defined above;

and MA signifies a mineral acid salt, with a disubstituted aminosulfur trifluoride of the formula $R^3R^4NSF_3$ wherein each $R^3$ and $R^4$, alike or different, is a primary alkyl group of 1-4 carbon atoms; or when taken together are —$(CH_2)_4$—, —$(CH_2)_5$— or —$CH_2CH_2OCH_2CH_2$—; at a temperature of about $-40°$ C. to about $+80°$ C.; in the presence of a polar or nonpolar solvent and recovering a fluorine containing compound. When $R^2$ is to be hydroxyl in the final product, the compound subjected to fluorination should have $R^2$ as the ester (or equivalent protective group) which is subsequently converted to the hydroxyl.

When the starting ketone is a mineral acid salt, e.g., hydrogen sulfate, good yields of the desired fluorinated compounds I are obtained.

For better yields it is preferred to use a starting ketone which is an amide. It is more preferred to use starting materials in which $R^3$ has 3-8 carbons.

When the amide starting material is used, the fluorination step produces an intermediate compound IV having the formula

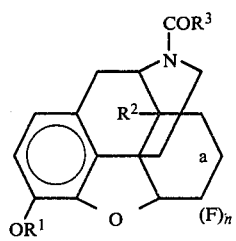

IV wherein $R^1$, $R^2$, $R^3$, a and n have the values previously mentioned. This intermediate is subjected to reduction wherein the —$NCOR^3$ group is converted to —$NCH_2R^3$. The reduction can be accomplished by usual chemistry, as for example, subjecting the intermediate IV to reaction with $LiAlH_4$, as exemplified in the examples below. Other reducing agents which can be used include alkali metal hydrides such as sodium or potassium borohydride.

The disubstitutedaminosulfur trifluorides are known compounds. Particularly useful are diethylaminosulfur trifluoride (DAST), pyrrolidinosulfur trifluoride, morpholinosulfur trifluoride and piperidylsulfur trifluoride.

The reaction is normally carried out in a solvent medium, preferably with use of a highly polar catalyst. The solvents can be polar or nonpolar but must be nonreactive with the aminosulfur trifluoride. Polar solvents tend to give more of the 6-fluoro-6,7-unsaturated codeines (n=1) while nonpolar solvents generally give more of the 6,6-difluoro compounds (n=2).

By polar solvent is meant a compound that has a high dielectric constant. Solvents which favor conversion of ketones to vinylene fluorides (>C=CF—) are polar and include dioxane, diethyl ether, tetrahydrofuran, ethylene glycol dimethyl ether, diethylene glycol dimethyl ether, and triethylene glycol dimethyl ether, etc. Nonpolar solvents such as hydrocarbons and halogenated hydrocarbons generally increase the amount of 6,6-difluoro (gem) compound formed.

The addition of a small amount of a strong acid as a highly polar catalyst, such as fuming sulfuric acid, increases the rate of formation of the 6,7-unsaturated-6-fluoride. Other useful catalysts are strong mineral acids that in the quantities used do not react with the carbonyl compound or with double bonds or other groups of the codeine-type compounds. Useful catalysts include perchloric, polyphosphoric, fluosulfonic acid, etc. The useful ones generally have a log Ka of more than about $-2$. The amount of catalyst is generally of the order of 0.001 to 1% by weight of the starting ketone. The catalyst is believed to function to increase the polarity of the reaction media and increase the rate.

The reaction is conducted under substantially anhydrous conditions. The reaction vessel is suitably glass but metal or ceramic containers can be used. The reaction is conducted at $-40°$ to about $+80°$ with the range $0°$ to $30°$ generally preferred. The time is dependent upon the reactants and the temperature, with times of from less than an hour to a week or more being useful. Pressure is not critical but ambient or autogenous pressure is preferred.

The fluoro compounds obtained can be separated from the reaction mixture by conventional procedures. Chromatography is a particularly useful procedure for separation and purification but crystallization, extraction, etc. can be used.

All temperatures reported herein are in °C.

BEST MODE

The best mode of practicing the invention is exemplified by Example 11.

EXAMPLE 1

17-Methyl-6,7-didehydro-4,5-epoxy-6-fluoro-3-methoxymorphinan Hydrochloride (2) and
17-Methyl-6,7-dihydro-4-hydroxy-5-chloro-6-fluoro-3-methoxymorphinan Hydrochloride (3)

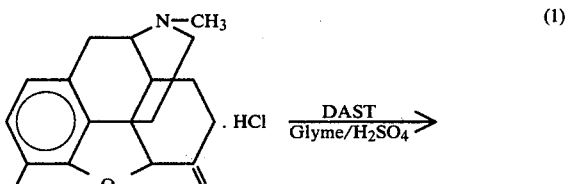

(1)

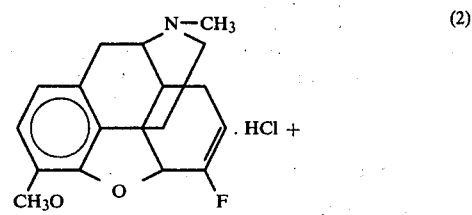

(2)

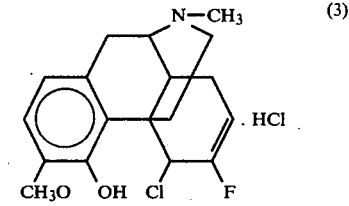

(3)

A solution of 40 ml of diethylaminosulfur trifluoride (DAST) in 160 ml of glyme was added dropwise to a suspension of 8.0 g of hydrocodone hydrochloride and 1.6 ml of fuming sulfuric acid in 240 ml of glyme cooled to $-78°$. The reaction mixture was warmed to room temperature and stirred for 8 days. The mixture was poured over ice, made basic with sodium bicarbonate and extracted with methylene chloride. Evaporation of the methylene chloride extracts gave a viscous oil which was taken in ether and filtered. Concentration of the ether filtrate gave 4.87 g of a white solid which was chromatographed on silica. Elution with 1/1 hexane/acetone containing 1% diethylamine, gave 0.58 g of white solid (2) melting at 167°–169° (HCl salt 214°–217°) and 2.09 g of white solid (3) melting at 169°–173° (HCl salt 178°–182°). The infrared spectrum showed =CF absorption at 5.91μ with no indication of C=O. $^{19}$F nmr (CDCl$_3$) for (3) δ −116.6 ppm for (2) δ −116.2 ppm.

HRMS (3) Calcd for $C_{18}H_{19}NO_2FCl$: 335.1089. Found: 335.1089.

Anal. Calcd for Cl: 19.05. Found: 19.04.

HRMS (2) Calcd for $C_{18}H_{20}NO_2F$: 301.1497. Found: 301.1432.

EXAMPLE 2

17-Methyl-4,5-epoxy-6,6-difluoro-3-methoxymorphinan Hydrochloride (4) and
17-Methyl-6,7-didehydro-4,5-epoxy-6-fluoro-3-methoxymorphinan (5)

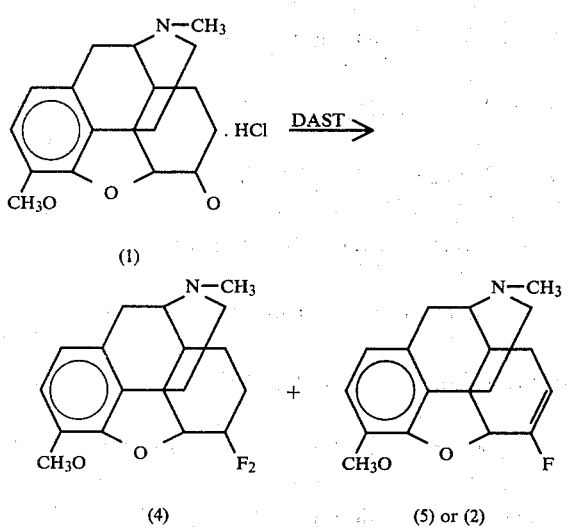

A mixture of 10.0 g (0.029 mole) of hydrocodone hydrochloride in 200 ml of CCl$_3$F (Freon ® 11) was cooled to −78°. To this was added dropwise a solution of 50 ml of diethylaminosulfur trifluoride (DAST) in 50 ml of CCl$_3$F. The mixture was warmed to room temperature, stirred for 5 days, then poured over crushed ice. The solution was made basic with sodium bicarbonate and separated. The aqueous layer was extracted with methylene chloride and the combined organic extracts were washed with water, then brine and dried (MgSO$_4$). This gave 8.65 g of the crude product as a viscous oil. A 1.6 g sample was fractionated by preparative chromatography to give 800 mg of the pure difluoro derivative (4). A sample converted to the hydrochloride salt melted at 270°–275°. $^{19}$F nmr (CDCl$_3$) δ −91.6, −94.2, −104.1 and −106.7 ppm.

The reaction mixture also contained minor amounts of the monofluoro-α,β-unsaturated compound (5).

EXAMPLE 3

17-Methyl-6,7-didehydro-4,5-epoxy-6-fluoro-3-hydroxymorphinan Hydrochloride (6)

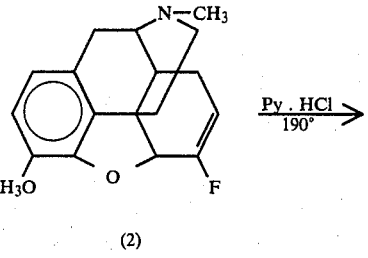

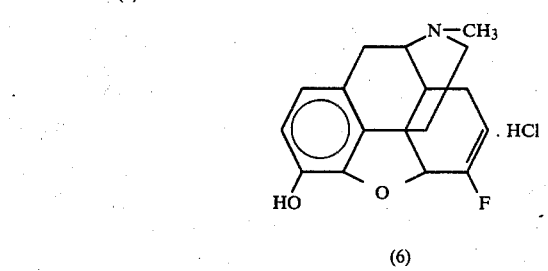

A mixture of 800 mg of the methoxy derivative 2 of Example 1 and 2.4 g of pyridine hydrochloride was heated at 190° for 3 hr, cooled and diluted with water. The aqueous solution was made basic with sodium hydroxide and extracted with methylene chloride. The methylene chloride extracts were dried (MgSO$_4$) and concentrated. The resulting oil was taken in ether and converted to the hydrochloride salt to give 200 mg of the O-demethylated derivative as a white crystalline solid. High performance liquid chromatography (HPLC) showed one major component (95%).

HRMS: Calcd for $C_{17}H_{18}NO_2F$: 287.1320. Found: 287.1320.

EXAMPLE 4

I.

17-Cyclobutylcarbonyl-4,5-epoxy-6,6-difluoro-3-methoxymorphinan (8) and
17-Cyclobutylcarbonyl-6,7-didehydro-4,5-epoxy-6-fluoro-3-methoxymorphinan (9)

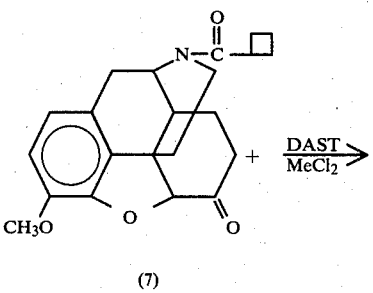

-continued

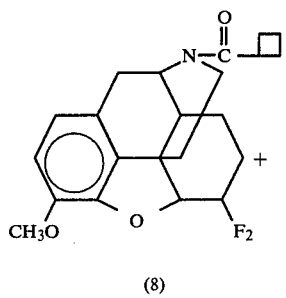

(8)

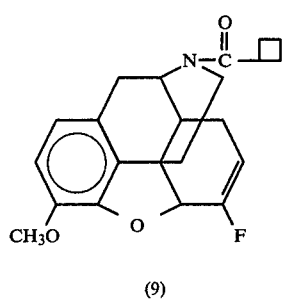

(9)

A solution of 25.0 g (68 mmoles) of the keto amid (7) prepared by reaction of cyclobutyl carbonyl chloride with the amine (19) as described in Example 7 in 200 ml of dry methylene chloride was cooled to −78°. To this was added dropwise a solution of 25 ml (200 mmoles) of DAST in 100 ml dry methylene chloride. The mixture was stirred at 25° for 6 days, poured onto crushed ice and neutralized, separated, washed with water then brine and dried over MgSo$_4$. The resulting oil was collected with ether to give 14.32 g of white solid. Concentration of the ether filtrate gave an additional 10.0 g of solid. $^{19}$F nmr (CLDl$_3$): δ−91.6, −94.2, −104.3 and −106.9 ppm (—CF$_2$) and −116.4 ppm (=CF).

II.

17-Cyclobutylmethyl-4,5-epoxy-6,6-difluoro-3-methoxymorphinan Hydrochloride (10)

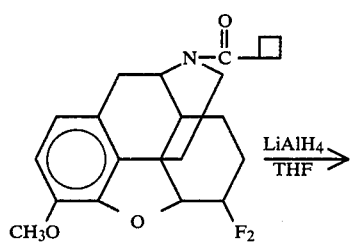

(8)

-continued

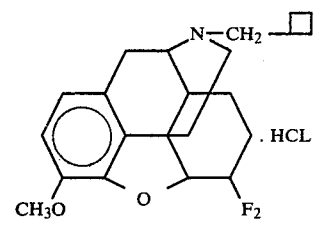

(10)

A mixture of 12.2 g of the amides from part I is 100 ml of anhydrous tetrahydrofuran was added dropwise to a stirred suspension of 4.5 g of LiAlH$_4$ in 200 ml of anhydrous tetrahydrofuran. The mixture was heated at reflux for 24 hr, cooled and then hydrolyzed using 4.5 ml water, 4.5 ml of 15% sodium hydroxide and 13.5 ml water. This gave 6.1 g of the crude amines. A 2.2 g sample was chromatographed on silica gel. Elution with methylene chloride containing 2% methanol and 1% diethylamine gave 1.5 g of 90% pure difluoride as a viscous oil. This was dissolved in ether and converted to the hydrochloride salt. $^{19}$F nmr (CDCl$_3$) δ−91.7, −94.3, −104.2 and −106.8 ppm (S). Infrared spectrum showed

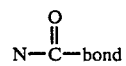

absent.

HRMS: Calcd for C$_{22}$H$_{27}$NO$_2$F$_2$: 375.2008. Found: 375.2003.

EXAMPLE 5

17-Cyclopropylmethyl-4,5-epoxy-6,6-difluoro-3-methoxymorphinan (15) and 17-Cyclopropylmethyl-6,7-didehydro-4,5-epoxy-6-fluoro-3-methoxymorphinan (16) and Hydrochlorides difluoride (13) and 6.8 g of about a 50:50 mixture of difluoride (13) and monofluoro (14).

A total of 7 g of the amide (13) was dissolved in 100 ml of tetrahydrofuran and mixed with 3 g of LiAlH$_4$ in 100 ml of tetrahydrofuran. After refluxing 16 hrs, 3 ml of water was added followed by 3 ml of 15% NaOH and

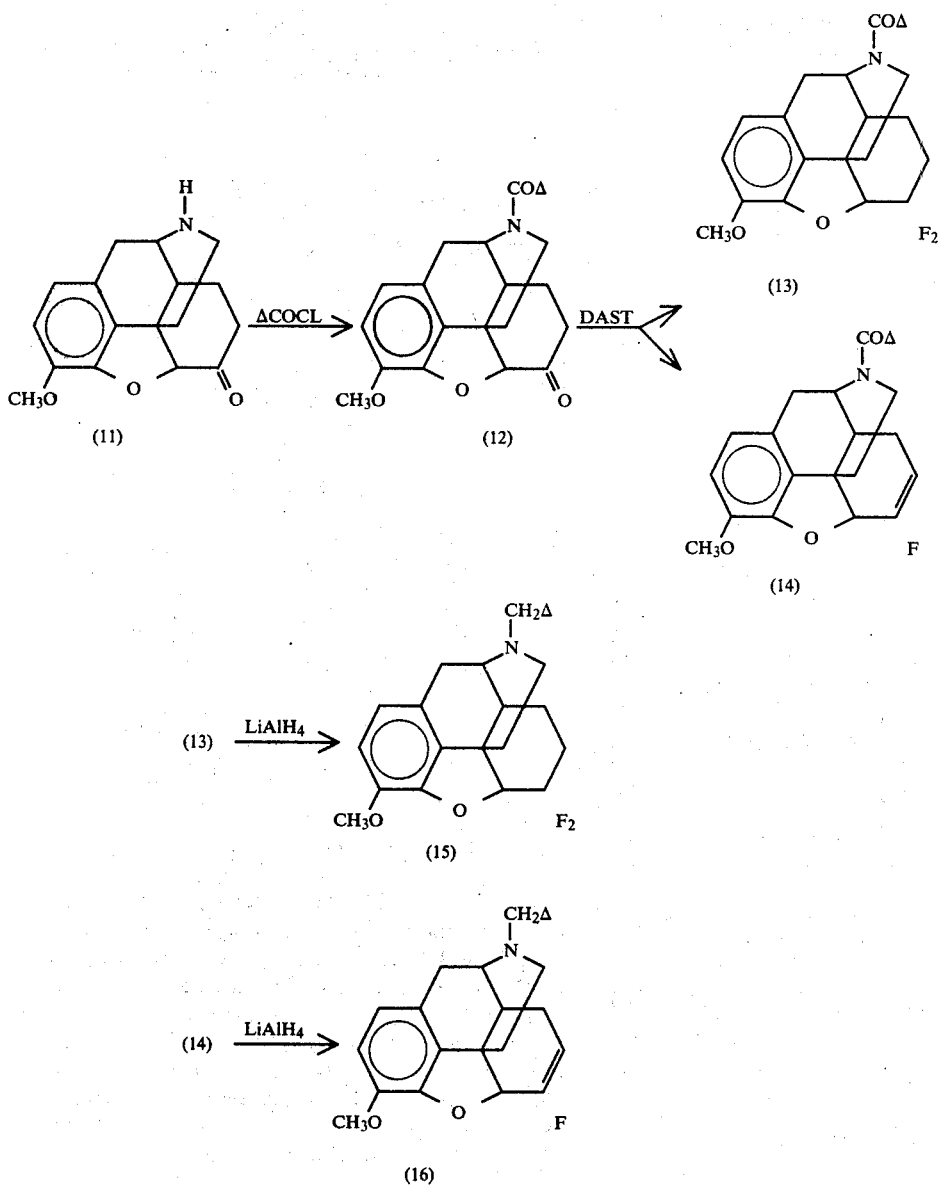

The N-cyclopropylcarbonylcodone (12) was obtained by reacting 18 g of cyclopropane carbonyl chloride with 30.7 g of the amine (11) at room temperature in methylene chloride in the presence of 20 g of tetraethylamine to yield 33 g of product as a white solid. These are identified by Gates, J. Med. Chem. 7, 127 (1964).

When 18.5 g of the amide (12) was dissolved in 150 ml of methylene chloride, cooled, and 18 ml of DAST added, after 3 days at room temperature, 19.2 g of a brown oil resulted. This was dissolved in ether, filtered and the oil chromatographed twice on silica using 90% ether-cyclohexanone with 1% methylene chloride and 0.001% water. There was obtained 4.2 g of 87% pure 9 ml of water to give 6.13 g of product which was chromatographed using 1:1 hexane: acetone containing 1% triethylamine to give 3.6 g of (15) in 96% purity by $^{19}$F nmr or 91% by HPLC as a white solid m.p. 69°–73°. The hydrochloride of the latter softened at 100° and had a mp of 123°–133°. HMRS Calcd: 361.1852; Found: 361.1846.

Ten g of codone amide (12) was dissolved in 120 ml of gylme, 0.8 ml sulfuric acid and 10 ml DAST in 80 ml of glyme added at −78°. After stirring at room temperature for 6 days, the mixture was poured on ice, neutralized, extracted with methylene chloride, evaporated and the residue dissolved in ether to give 10.2 of the 6-fluoro morphinan (14) which was chromatographed on silica using 90% ether-hexane with 1% methylene chloride and 0.1% water. About 2.3 g of this product was dissolved in 50 ml of tetrahydrofuran and reduced with 1.1 g of LiAlH$_4$ in 50 ml of tetrahydrofuran by refluxing 16 hrs. There was obtained 1.4 g of white product (16) as the HCl salt, mp 93°–97°.

EXAMPLE 6

17-Cyclopropylmethyl-4,5-epoxy-6,6-difluoro-3-hydroxymorphinan (17) and Hydrochloride

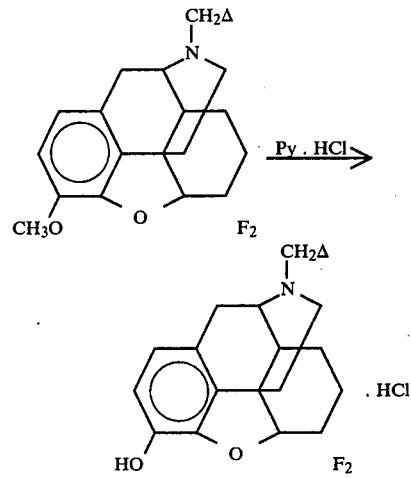

When 2.8 g of the O-methyl ether (compound (15) of Example 5) was heated at 190°–195° for 3 hrs with 7 g of pyridine hydrochloride, diluted with water, extracted with methylene chloride, then dissolved in toluene, filtered, concentrated, dissolved in ether and crystallized from ether-hexane by adding hexane, the resultant white powder (1 g) mp 78°–84° was converted to the HCl salt and purified by HPLC (96% pure), mp 312°–317°.

HRMS Calcd: 347.1695; Found: 347.1708.

EXAMPLE 7

17-Cyclopropylmethyl-6,7-didehydro-4,5-epoxy-6-fluoro-3-hydroxymorphinan Hydrochloride (18)

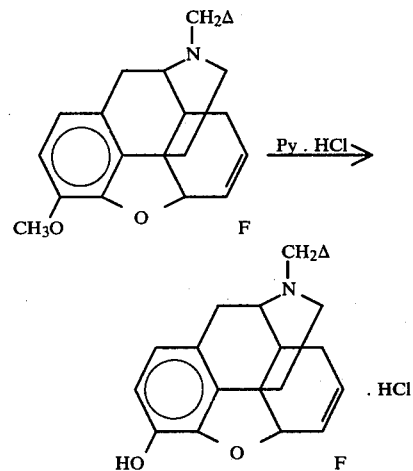

When 2.9 g of the O-methyl ether )compound (16) of Example 5) was reacted with 7 g of pyridine hydrochloride as in Example 6, there was obtained a tan solid which was taken up in ether and converted to the hydrochloride salt. The salt was recrystallized from ethanol to give 0.6 of white solid (18) mp 285°–290°. HPLC showed one major peak (94.9%). HRMS: Calcd for C$_{20}$H$_{22}$ONF$_2$: 327.1627. Found: 327.1598.

EXAMPLE 8

17-Allyl-4,5-epoxy-6,6-difluoro-3-methoxymorphinan (20) and
17-Allyl-6,7-didehydro-4,5-epoxy-6-fluoro-3-methoxymorphinan (21) and Hydrochlorides

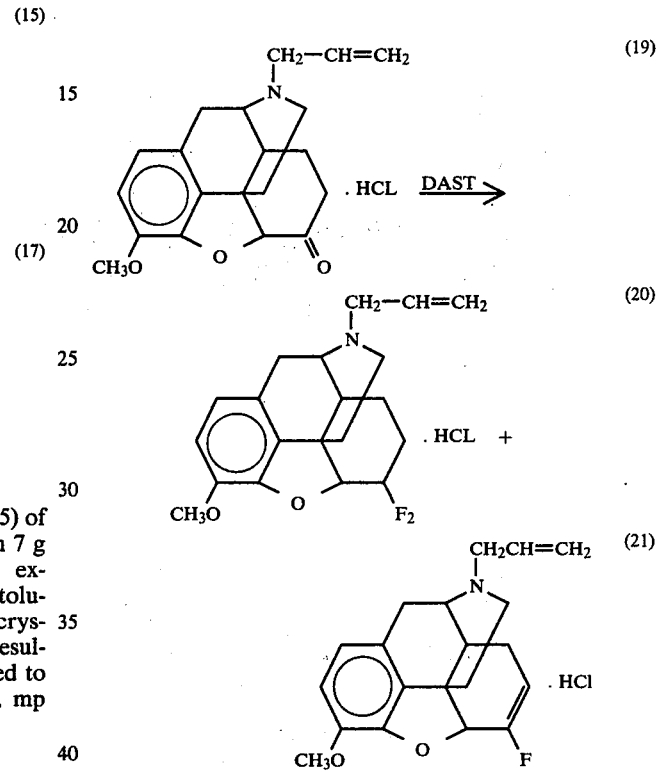

To 10 g of amine (11) of Example 5 in 150 ml of dimethylformamide was added 4 g of allyl bromide and 2.8 g of NaHCO$_3$. The mixture was heated at 80°–85° for 5 hrs, diluted with water, extracted with ether and converted to 12.7 g of the amine salt (19) above. The salt was reacted with diethylaminosulfur trifluoride according to the process of Example 2 and the hydrochloride salts formed are separated by chromatography as described in Example 5. $^{19}$F mnr (CDCl$_3$): δ −91.6, −94.2, −104.1 and 106.7 ppm.

EXAMPLE 9

A.

17-Cyclobutylcarbonyl-4,5α-epoxy-6-keto-14β-acetyl-3-methoxymorphinan (23)

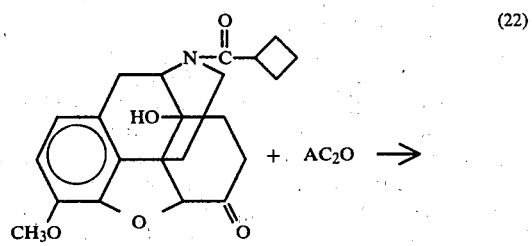

-continued

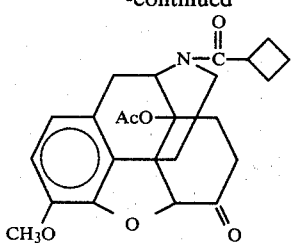
(23)

A solution of 23.0 g of the morphinan (22) in 100 ml of acetic anhydride was heated at reflux for 0.5 hr, cooled and then concentrated. The residue was dissolved in 200 ml of water, cooled to 0° and adjusted to pH 9 with ammonium hydroxide. A viscous oil precipitated. The water layer was decanted and the oil was dissolved in methylene chloride and dried over $Na_2SO_4$. Concentration of the methylene chloride gave 22.3 g of viscous oil. The infrared spectrum showed essentially no $OH^-$ absorption.

B.
Cyclobutylcarbonyl-4,5α-epoxy-6,6-difluoro-14β-acetyl-3-methoxymorphinan (24) and 17-Cyclobutylcarbonyl-6,7-didehydro-4,5α-epoxy-6-fluoro-14-acetyl-3-methoxymorphinan (25)

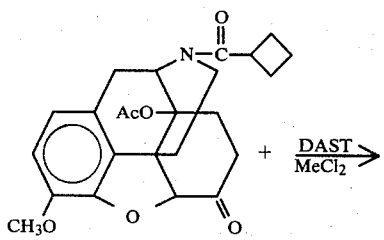
(23)

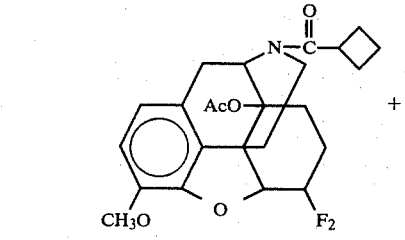
(24)

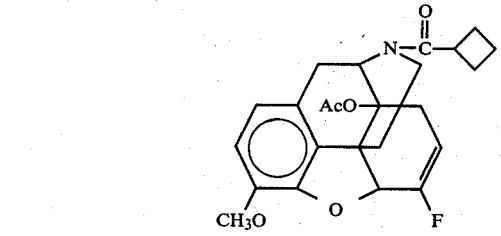
(25)

A solution of 18.0 g of the ketoamide (23) in 150 ml dry methylene chloride was cooled to −78°. A solution of 18 ml of DAST in 150 ml of methylene chloride was added dropwise. The reaction mixture was stirred at room temperature for three days, poured over ice and neutralized with sodium bicarbonate. The organic layer was separated, washed with brine and dried ($K_2CO_3$). This gave 16.6 g of the crude fluorides as a viscous oil. The HRMS of the crude sample showed:

$C_{24}H_{27}NO_5F_2$ Calcd. 447.1856. Found 447.1846.
$C_{24}H_{26}NO_5F$ Calcd. 427.1793. Found 427.1752.

The fluoro derivatives were separated using HPLC. Elution with hexane-acetone-triethylamine gave 8 g of the difluoride (24) as a colorless viscous oil. $^{19}F$ nmr ($CDCl_3$) δ−91.3, −93.9 and 102.3, 104.4 ppm (—$CF_2$).

C.
17-Cyclobutylmethyl-4,5α-epoxy-6,6-difluoro-14β-hydroxy-3-methoxymorphinan Hydrochloride (26)

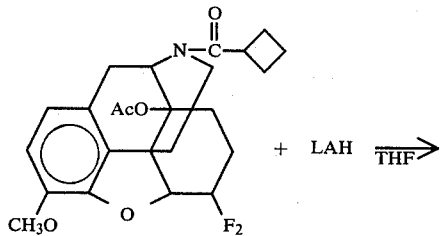
(24)

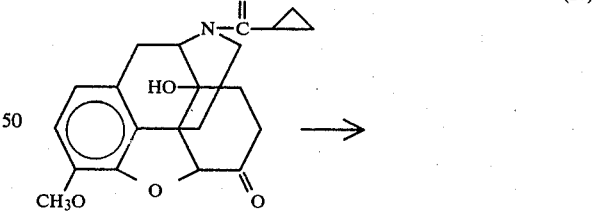
(26)

An 8 g sample of the difluoro amide (24) was reduced as in Example 3, II. This gave 4.5 g of tan solid which was dissolved in ether and some insoluble solid was filtered. Concentration of the ether soluble material gave 2.6 g of pale yellow solid which was taken in ether and decolorized by use of charcoal to give a white solid melting at 162°–164°. When converted to the hydrochloride salt (ether) the difluoro morphinan (26) melted at 266°–269°. Its infrared spectrum shows hydroxyl band at 3400 $cm^{-1}$ but no amide or carbonyl absorption.

EXAMPLE 10

17-Cyclopropylmethyl-4,5α-epoxy-6,6-difluoro-14β-hydroxy-3-methoxy morphinan Hydrochloride (28)

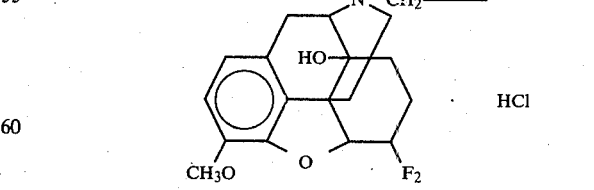
(27)

(28)

This compound was prepared using the procedure outlined above starting with (27) and acetylating, fluorinating with DAST, recovering the difluoride and hydrolyzing and reducing as in Example 9 to give the hydrochloride salt, (28) which melted at 248°–252°.

Anal. Calcd for $C_{24}H_{25}NO_3F_2$: C, 66.83; H, 6.68 N, 3.71. Found: C, 66.47; H, 6.64 N, 3.97.

EXAMPLE 11

17-Cyclopropylmethyl-6,7-didehydro-4,5α-epoxy-6-fluoro-3-acetoxymorphinan (29)

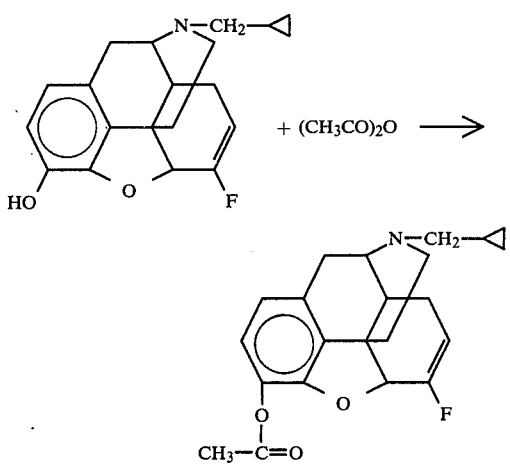

A solution of 3.0 g of the crude phenol (18) of Example 7 in 25 ml of acetic anhydride was heated at reflux for 0.5 hr then concentrated. The residue was treated with ice water and made basic with ammonia. The aqueous base was extracted with methylene chloride, treated with decolorizing charcoal and dried ($K_2CO_3$). Removal of the solvent gave 3.6 g of tan oil which was recrystallized from hexane-ether to give 0.84 g of the acetoxy derivative as a white solid melting at 86°–88°. The infrared spectrum showed strong carbonyl absorption at 1730 cm.

Anal. Calcd. for $C_{22}H_{24}NO_3F$: C, 71.53; H, 6.45; N, 3.79. Found: C, 71.59; H, 6.64; N, 3.75.

A sample of the base was dissolved in ether and converted to the hydrochloride salt, which melted at 139° (dec.).

EXAMPLE 12

17-Cyclopropylmethyl-4,5α-epoxy-6,6-difluoro-3-acetoxymorphinan (30)

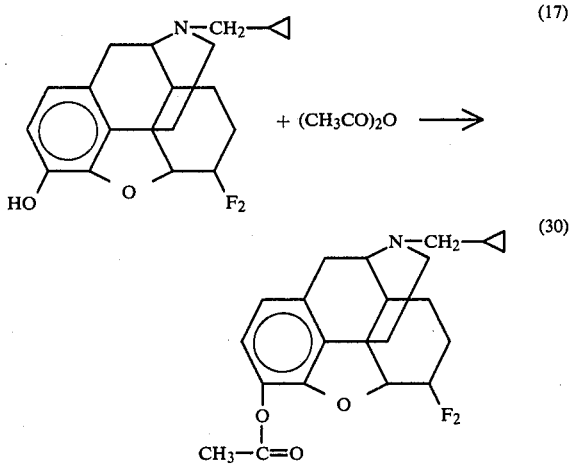

The procedure of Example 11 was used to prepare the acetoxy derivative of the corresponding difluoride.

The difluoride (30) was obtained as a white solid melting at 128°–130°.

Anal. Calcd. for $C_{22}H_{25}NO_3F_2$: C, 67.85; H, 6.47; N, 3.60. Found: C, 67.23; H, 6.42 N, 3.52.

HRMS Calcd.: 389.1801. Found: 389.1842.

EXAMPLE 13

6-Fluoro-(32) and 6,6-difluorodihydronorcodeinone (33)

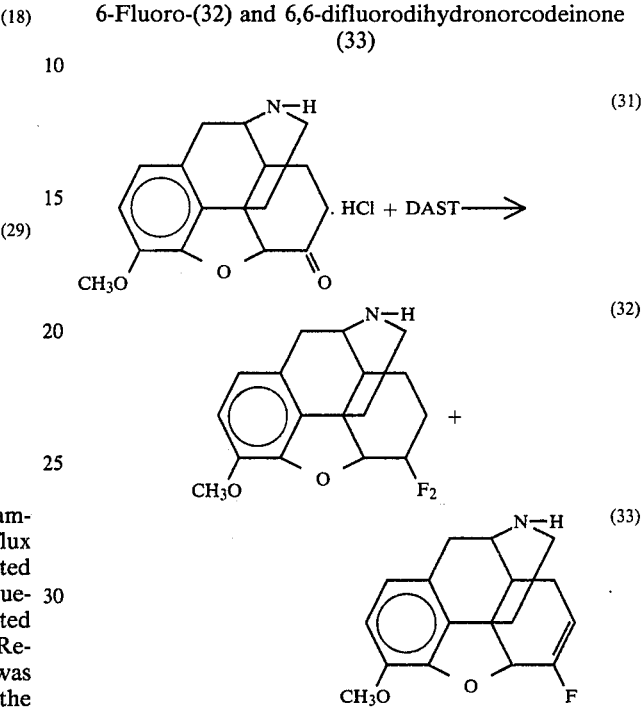

A mixture of 13.5 g of the nordihydrocodeinone hydrochloride (31) in 250 ml of methylene chloride was treated with 13 ml of DAST as previously described. After work-up the residue was taken in ether and filtered. This gave 6.7 g of a mixture of the fluoro derivatives as a tan solid. These compounds are separated by chromatography as described in Example 1. $^{19}F$ nmr −93.13, −105.57 ppm (difluoride) and −116.12 ppm (vinyl).

HRMS calcd. for $C_{17}H_{19}NO_2F_2$: 307.1383. Found: 307.1353.

HRMS calcd. for $C_{17}H_{18}NO_2F$: 287.1320. Found: 287.1292.

The fluoronorcodeinones (32) and (33) of Example 13 are valuable intermediates to N-substituted compounds where the R group is as previously defined. Thus, alkylation with RX where X is Cl or Br in a solvent in the presence of a base gives the N—R compound. Suitable alkylating agents are cyclohexylmethyl bromide, dimethylallyl chloride, 2-thienylmethyl chloride, p-methoxyphenethyl bromide, cyclopropylmethyl chloride, etc. which give the corresponding N-cycloalkylmethyl, allylic, thienylmethyl or phenethyl derivatives.

When the general procedure of foregoing Examples 4 and 5 is applied to compounds corresponding to (7) and (12) but where $R^3$ is $CH_2C_6H_5$ $C_6H_{11}$, or $—(CH_2)_9H$ there are obtained the corresponding compounds, e.g., N-phenethyl-6,7-didehydro-4,5α-epoxy-6-fluoro-3-methoxymorphinan, N-phenethyl-4,5α-epoxy-6,6-difluoro-3-methoxymorphinan and the N-cyclohexylmethyl or N-n-decyl morphinans.

Starting with N-butyl or N-dimethylallylcodeine and using the process of Examples 1 and 2 there results the corresponding butyl and dimethylallyl derivatives. Similarly N-furanylmethyl, thienylmethyl and thienylethyl compounds corresponding to those of Example 5 can be prepared and used as described above.

N-cyclobutanoylnoroxycodone-14-acetate is used according to the general procedure of Example 9, to give both 6,6-difluoro- and 6-fluoro-$\Delta$6,7-cyclobutylmethylnoroxycodone-14-acetate. Hydrolysis of the latter gives the 14-hydroxy compounds. The corresponding 14-butanoyl, propionyl and formyl can be prepared by suitable acylation of the 14-hydroxy compounds with alkanoyl halides.

In the compounds as obtainable by the above procedures, the 3-position is generally the 3-methoxy. Treatment of these compounds with demethylating agents such as hydrogen halides gives the 3-hydroxy from which alkyl ethers of up to 4 carbons, e.g., ethoxy, propoxy or butoxy, or esters of $C_1$-$C_{12}$ alkanoic acids, e.g. formate, butyrate, dodecanoate, etc., can be obtained by general synthetic methods. The esters can exhibit greater potency as pharmaceuticals.

Pharmaceutical Salts

Pharmaceutically suitable acid addition salts of these compounds include those made with physiologically acceptable acids that are known in the art; such salts include hydrochloride, sulfate, phosphate, nitrate, citrate, maleate, and the like.

Utility

The N-substituted compounds of this invention are active pharmaceutically as analgesics and/or narcotic antagonists. The unsubstituted (NH) 6-fluoro compounds are useful as intermediates to the active pharmaceuticals.

Dosage Forms and Use

The compounds of this invention can be administered as analgesic agents to alleviate pain or as narcotic antagonists by any means that produces contact of the active agent with the agent's site of action in the body of a mammal. They can be administered either as individual therapeutic agents or in a combination of therapeutic agents, generally with a pharmaceutical carrier. The dosage depends upon the pharmacodynamic characteristics of the particular agent, and its mode and route of administration; age, health, and weight of the recipient; nature and extent of symptoms; kind of concurrent treatment; frequency of treatment; and the effect desired. Usually a daily dosage of active ingredient can be about 0.05 to 100 milligrams per kilogram of body weight in divided doses 2 to 4 times a day or in sustained release form.

Dosage forms (compositions) suitable for internal administration can contain from about 25 milligrams to about 75 milligrams of active ingredient per dosage unit. In these pharmaceutical compositions the active ingredient will ordinarily be present in an amount of about 0.5-95% by weight based on the total weight of the composition.

The active ingredient can be administered orally in solid dosage forms such as capsules, tablets, and powders, or in liquid dosage forms such as elixirs, syrups and suspensions; it can also be administered parenterally in sterile liquid dosage forms; or rectally in the form of suppositories.

Capsules or tablets contain the active ingredient and powdered carriers, such as lactose, sucrose, mannitol, starch, cellulose derivatives, magnesium stearate, stearic acid, and the like and can be manufactured as sustained release products.

In general, water, a suitable oil, saline, aqueous dextrose (glucose) and related sugar solutions, and glycols such as propylene glycol or polyethylene glycols, are suitable carriers for parenteral solutions. Solutions for parenteral administration contain preferably a water soluble salt of the active ingredient, e.g., hydrochloride; suitable stabilizing agents; buffer substances; antioxidizing agents such as ascorbic acid; and preservatives such as benzalkonium chloride, methyl- or propyl-paraben and chlorobutanol.

Suppositories contain the active ingredient in a suitable oleaginous or water-soluble base. The oleaginous class includes cocoa butter and fats having similar properties; the water-soluble class includes polyethylene glycols.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 50 milligrams of powdered active ingredients, 110 milligrams of lactose, 32 milligrams of talc and 8 milligrams magnesium stearate.

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by filtration.

Another parenteral composition suitable for administration by injection is prepared by dissolving 1% by weight of active ingredient in sodium chloride injection U.S.P. XV and adjusting the pH of the solution to between 6 and 7. The solution is sterilized by filtration.

Suspension

An aqueous suspension is prepared for oral administration so that each 5 milliliters contain 10 milligrams of finely divided active ingredient, 500 milligrams of acacia, 5 milligrams of sodium benzoate, 1.0 gram of sorbitol solution, U.S.P., 5 milligrams of sodium saccharin and 0.025 milliliters of vanilla tincture.

Test Results

A standard procedure for detecting and comparing the analgesic activity of compounds in this series for which there is good correlation with human efficacy is the standard phenylquinone writhing test modified from Siegmund, et. al., *Proc. Soc. Exp. Biol. Med.* 95, 729 (1957). A test compound suspended in 1% methylcellulose was given orally to fasted (17–21 hours) female white mice, 5–20 animals per double blind test. Aqueous (0.01% phenyl-p-benzoquinone) phenyl-quinone was injected intraperitoneally at 24 minutes later using 0.20 ml per mouse. Commencing at 30 minutes after the oral administration of the test compound, the mice were observed for 10 minutes for a characteristic stretching or writhing syndrome which is indicative of pain induced by phenylquinone. The effective analgesic dose for 50% of the mice (ED 50) was calculated by the moving average method of Thompson, U.R., *Bact. Rev.* 11 115–145 (1947). This is reported as PQW $ED_{50}$ in the table below.

Some of the compounds of this invention are particulary useful as analgesics by subcutaneous injection, e.g. compound (29) of Example 11 had an $ED_{50}$ of 0.0016 fifteen minutes after injection.

Narcotic analgesics produce in mice an erection and arching of the tail (90° or more) which is referable to spinal cord stimulation. This Straub tail reaction is not produced by other analgesics, including the narcotic antagonists.

The method used was modified from Shemano (Shemano, I., and Wendel, H., *Tox. Appl. Pharm.* 6, 334-9 (1964)). $CF_1S$ female mice (18–21 g), 10–20 mice per dose were injected subcutaneously with log scaled doses of analgesic in 0.9% saline or 0.45% saline containing 0.5% methylcellulose. A positive Straub tail response was recorded if a tail was erected for 3 seconds at any time within 25 minutes after dosing. A quantal Straub tail $ED_{50}$ was calculated by the moving average method and is an indication of physical dependence.

The narcotic antagonist (anti-Straub tail) property of the compounds is estimated by their ability to prevent morphine-induced Straub tail in mice. In this test the compound is injected intraperitoneally into mice and 10 minutes later 53 mg/kg of morphine sulfate is given subcutaneously. Prevention of the induction of a 90° Straub tail for minutes after the morphine sulfate injection is considered to indicate narcotic antagonism in the compound tested.

The following table shows the activity in mg/kg exhibited by various compounds including those of this invention (in the hydrochloride salt form to provide solubility), when tested by the procedures given above. A value of 135 mg/kg or higher is considered to indicate an inactive compound.

| Example | Compound Number | Mouse $ED_{50}$ Values | | |
|---|---|---|---|---|
| | | POW | Straub Tail | Antistraub Tail |
| 1 | 2 | 8.5 | 26.0 | 94.0 |
| 2 | 4 | 2.7 | 10.0 | >81.0 |
| 3 | 6 | 8.0 | 17.0 | N.T. |
| 4 | 10 | 2.9* | >81.0 | 4.1 |
| 5 | 15 | 2.2* | >54.0 | 0.15 |
| 5 | 16 | 18.0 | >135.0 | 0.21 |
| 6 | 17 | 2.6* | >54.0 | 0.003 |
| 7 | 18 | 7.2 | >135.0 | 0.18 |
| 9 | 26 | 26.0 | >135.0 | 10.8 |
| 11 | 29 | 1.3 | >18 | 0.0022 |
| 12 | 30 | 2.2 | >18 | 0.0031 |
| Codeine $PO_4$ | | 4.7* | 202.0 | >140.0 |
| Morphine $SO_4$ | | 3.0* | 48.0 | N.T. |
| Ayer 3,137,701 (6-fluoro-7,8 double bond) | | 32.0 | 63.0 | >162.0 |

N.T. = Not Tested.
*Peak time value (i.e., maximum activity within 30 min of administration).

The Straub Tail Antagonism test was modified by giving test drugs (in 1% methyl cellulose with 1.25% "Tween 80") subcutaneously, followed by intraperitoneal injection of morphine sulfate (at 35 mg/kg) 5 minutes after the test drug. After 15 minutes, the animals were observed for 5 minutes for evidence of Straub tail. ED 50's were calculated as above with a 95% confidence limit as described by Litchfield, J. Pharmacol. Exp. Ther. 96, 99 (1949). When compound #17 (Example 6) was tested the ED 50 was 0.0033 mg/kg. The value for Pentazocine was 1.9 mg/kg.

We claim:

1. A compound of the formula

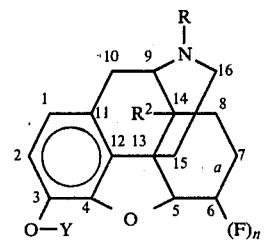

wherein
R is selected from the group consisting of hydrogen, alkyl of 1-10 carbons, allyl, methylallyl, dimethylallyl, cycloalkylmethyl of 4–7 carbon atoms, 2-furanylmethyl, 2-tetrahydrofuranylmethyl, 2-thienylmethyl, 2-thienylethyl and phenylethyl which may be ring substituted with chloro, bromo, fluoro, methoxy or 1-3 carbon alkyl substituents;
Y is H or R';
R' is selected from the group consisting of alkyl of 1-4 carbons and alkanoyl of 1-12 carbons;
$R^2$ is selected from the group consisting of hydrogen, hydroxy and alkanoate of 1-4 carbons;
n is 1 or 2; and
a is a 6,7 double bond when n=1, and a single bond when n=2;
and pharmaceutically acceptable salts of the compound.

2. A compound of claim 1 which is 17-methyl-6,7-didehydro-4,5-epoxy-6-fluoro-3-methoxymorphinan.

3. A compound of claim 1 which is 17-methyl-4,5-epoxy-6,6-difluoro-3-methoxymorphinan.

4. A compound of claim 1 which is 17-methyl-6,7-didehydro-4,5-epoxy-6-fluoro-3-methoxymorphinan.

5. A compound of claim 1 which is 17-methyl-6,7-didehydro-4,5-epoxy-6-fluoro-3-hydroxymorphinan.

6. A compound of claim 1 which is 17-cyclobutyl-methyl-4,5-epoxy-6,6-difluoro-3-methoxymorphinan.

7. A compound of claim 1 which is 17-cyclopropyl-methyl-6,7-didehydro-4,5α-epoxy-6-fluoro-3-acetoxymorphinan.

8. A compound of claim 1 which is 17-cyclobutyl-methyl-4,5α-epoxy-6,6-difluoro-3-acetoxymorphinan.

9. A compound of claim 1 which is 17-cyclopropyl-methyl-4,5-epoxy-6,6-difluoro-3-methoxymorphinan.

10. A compound of claim 1 which is 17-cyclopropyl-methyl-6,7-didehydro-4,5-epoxy-6-fluoro-3-methoxymorphinan.

11. A compound of claim 1 which is 17-cyclopropyl-methyl-4,5-epoxy-6,6-difluoro-3-hydroxymorphinan.

12. A compound of claim 1 which is 17-cyclopropyl-methyl-6,7-didehydro-4,5-epoxy-6-fluoro-3-hydroxymorphinan.

13. A compound of claim 1 which is 17-allyl-4,5-epoxy-6,6-difluoro-3-methoxymorphinan.

14. A compound of claim 1 which is 17-allyl-6,7-didehydro-4,5-epoxy-6-fluoro-3-methoxymorphinan.

15. The compound of claim 1 in a pharmaceutical carrier in an amount of about 0.5 to 95% by weight based on the total weight of the composition.

16. A compound of claim 1 which is 17-cyclobutyl-methyl-4,5α-epoxy-6,6-difluoro-14α-hydroxy-3-methoxymorphinan hydrochloride.

17. A compound of claim 1 which is 17-cyclopropyl-methyl-4,5α-epoxy-6,6-difluoro-14α-hydroxy-3-methoxymorphinan hydrochloride.

18. A compound of claim 1 where R is cyclopropyl-methyl.

19. A compound of claim 1 where R is cyclobutyl-methyl.

* * * * *

UNITED STATES PATENT OFFICE
CERTIFICATE OF CORRECTION

PATENT NO. : 4,241,065
DATED : December 23, 1980
INVENTOR(S) : George A. Boswell, Jr.
Rosetta M. Henderson It is certified that error appears in the above-identified patent and that said Letters Patent are hereby corrected as shown below:

Column 22, line 7, "methyl-4,5α-epoxy-6,6-difluoro-14α-hydroxy-3-" should be --methyl-4,5α-epoxy-6,6-difluoro-14β-hydroxy-3---.

Column 22, line 10, "methyl-4,5α-epoxy-6,6-difluoro-14α-hydroxy-3-" should be --methyl-4,5α-epoxy-6,6-difluoro-14β-hydroxy-3---.

Signed and Sealed this

Twenty-third Day of June 1981

[SEAL]

Attest:

RENE D. TEGTMEYER

Attesting Officer  Acting Commissioner of Patents and Trademarks